US005399723A

United States Patent [19]
Iinuma et al.

[11] Patent Number: 5,399,723
[45] Date of Patent: Mar. 21, 1995

[54] ANTI-MRSA COMPOUND

[75] Inventors: Munekazu Iinuma; Hironori Tsuchiya; Masaru Sato; Shu Fujiwara, all of Gifu, Japan

[73] Assignee: Tsujimoto Kagaku Kogyo Co., Ltd., Osaka, Japan

[21] Appl. No.: 55,966

[22] Filed: Apr. 30, 1993

[30] Foreign Application Priority Data

Feb. 1, 1993 [JP] Japan .................. 5-037507

[51] Int. Cl.$^6$ ........................... C07D 311/74
[52] U.S. Cl. ........................................ 549/403
[58] Field of Search ........................ 549/403

[56] References Cited
FOREIGN PATENT DOCUMENTS
3246291 11/1991 Japan .................. 549/403

*Primary Examiner*—Alan L. Rotman
*Assistant Examiner*—A. A. Owens
*Attorney, Agent, or Firm*—Thompson, Hine And Flory

[57] ABSTRACT

An anti-MRSA compound comprising of the formula

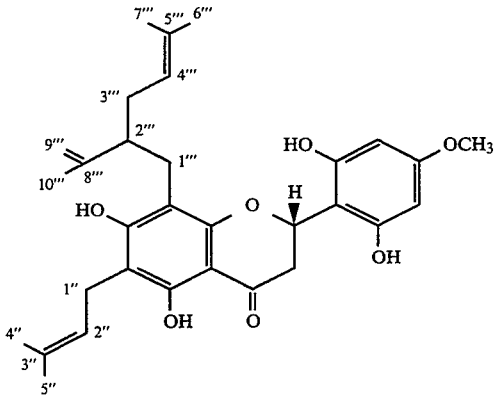

which is generally extracted from the root of *Sophora exigua*. The usage of this compound is for methicillin-resistant *Staphylococcus aureus*.

1 Claim, No Drawings

ANTI-MRSA COMPOUND

BACKGROUND OF THE INVENTION

1. Field of the Invention

The present invention relates to a novel compound having outstanding antibacterial activity against methicillin-resistant *Staphylococcus aureus* (herein-after referred to briefly as MRSA).

2. Description of the Prior Art

MRSA infection in hospitals has recently been a matter of serious concern. Since the major routes of MRSA infection are already known, this infection may be substantially controlled by instituting pertinent preventive measures. However, the incidence of MRSA among *Staphylococcus aureus* strains detected in large hospitals in Japan these days is more than 60 percent on the average. Furthermore, MRSA infection is spreading all over the country without geographic partiality. Consequently, the preventive measures taken today against the emergence of MRSA are actually inadequate. Moreover, once man is infected with MRSA, antibiotic therapy cannot be an effective remedy and the risk for death is astoundingly high. Vancomycin, for instance, is an antibiotic which is comparatively active against MRSA but it is certain that, being one of resistant bacteria, MRSA will acquire resistance to vancomycin, too, in a not-too-distant future.

SUMMARY OF THE INVENTION

In view of the above characteristics of resistance in MRSA, the inventors of the present invention had embarked on an extensive exploration of the vegetable kingdom for new substances having antibacterial activity. It is known that although they are scarcely contained or not contained at all in intact plants, a group of substances called phytoalexins are produced de novo and in significant quantities at sites of infection with pathogenic microorganisms or at sites subjected to physical injury or other stress. Thus, phytoalexins having antimicrobial activity are produced preferentially in the roots of plants which are high in the frequency of contact with pathogenic microorganisms and hence are favorite sites of infection. Consequently, in order that an antimicrobial principle may be screened out from among secondary metabolites of plants, it is rewarding to land on this mechanism of production of phytoalexins. Based on this concept, the inventors of the present invention sought antimicrobial activity against resistant *Staphylococcus aureus* bacteria.

The anti-MRSA compound of the invention has the following chemical formula.

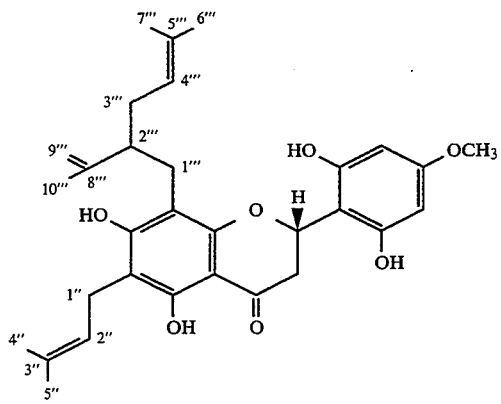

This compound was extracted from the root of *Sophora exigua* Criab, a deciduous shrub native to Thailand. The extraction procedure comprised drying the root of *S. exigua*, extracting about 90 g of the resulting powder with three 200 ml portions of acetone under reflux in a 500 ml egg plant-shaped flask, and concentrating the pooled acetone extracts under reduced pressure to provide about 5 g of acetone extract.

In the exploratory research which led to completion of the invention, acetone extracts were also prepared from *Sophora tonkinensis* and *Sophora flavescens*, both of which are plants of the same genus *Sophora*. Using three kinds of crude acetone extracts, inclusive of the above-mentioned extract of the invention, a primary screening was carried out for antibacterial activity against MRSA. As a result, specific activity could be detected only in the acetone extract of the root of *Sophora exigua*. The inventors thus confirmed the existence of anti-MRSA activity in the root of *Sophora exigua*.

Then, 5 g of the active acetone extract of *Sophora exigua* root was redissolved in 10 ml of acetone, blended with 10 g of silica gel and chromatographed on 150 g of silica gel. This chromatographic fractionation was carried out using a column, 30 mm dia.×70 cm long, and, as the eluent, chloroform-methanol on an ascending methanol gradient. The eluate was collected in about 50 ml fractions under TLC (thin-layer chromatography) monitoring. As a result, the objective activity was obtained in fractions 1 to 6. These fractions were respectively concentrated to 50 µg/ml and assayed for activity against a plurality of MRSA strains. Consequently, as shown in Table 1, strong activity was found in fraction 1 and slight activity in fractions 2 and 3. In the table, + represents 100% activity, — no activity, and ± intermediate activity.

Then, using the active fractions 1 to 3, the concentration dependence of activity was investigated. Thus, a dilution series of 100, 50, 25 and 12.5 µg/ml was prepared from each fraction and the MIC assay was carried out using MRSA and methicillin-sensitive *Staphylococcus aureus* (MSSA) strains. The results are set forth in Tables 2 to 4. The data on fraction 1 are presented in Table 2, that on fraction 2 in Table 3, and that on fraction 3 in Table 4.

Fraction 1 completely inhibited growth of MRSA at 50 µg/ml and higher concentrations and showed some activity even at the concentration of 25 ug/ml. Against MSSA, too, fraction 1 showed positive activity except against the tester strain IFO3761. However, since the conventional antibiotics have sufficient activity against MSSA, there is no problem with the inactivity against the tester strain IFO3761. On the other hand, fractions 2 and 3 were only slightly active even at the concentration of 100 μg/ml and showed no activity at all at lower concentrations.

Based on the above results, it was concluded that the activity against MRSA and MSSA existed only in fraction 1 and the isolation and structural identification of the activity were then performed.

The isolation method was as follows. Fraction 1 was purified by silica gel chromatography (chromatographic column, 20 mm dia. ×50 cm long; eluent: n-hexane-acetone on an ascending acetone gradient) in otherwise the same manner as described hereinbefore. As a result, three substances tentatively named Fr4-1-1, Fr4-1-2 and Fr4-1-3 were isolated. The minimal inhibitory concentrations (MICs) of these three substances in pure form were determined using MRSA and MSSA tester strains. As a result, the highest activity was exhibited by Fr4-1-1. The assay data are shown in Table 5.

The minimal inhibitory concentration, though it is dependent on tester strains used, was 3.124 against the tester strain G47 of MRSA and 1.563 against the tester strain TAZAKI of MSSA. Thus, very high activity was found against both resistant and sensitive strains. For reference's sake, the corresponding minimal inhibitory concentrations of four known antibiotics are shown in Table 6. It is seen that Fr4-1-1 is more active than gentamicin and vancomycin. In the table, DMPPC stands for methicillin, MPIPC for oxacillin, GM for gentamicin and VCM for vancomycin.

Fr4-1-1, obtained as a yellowish solid, was positive with both Gibbs and FeCl$_3$ reagents. In the HR-mass spectrum, 2 gave a [M]+ at m/z 522.2597, and the molecular formula corresponds to $C_{31}H_{38}O_7$. In the $^1$H Nmr spectrum, three one-proton double doublets were observed at δ5.93 (J=14, 3 Hz), 3.85 (J=17, 14 Hz) and 2.51 (J=17, 3 Hz) which were assignable to H-2 and H-3 of a 2′,6′-dioxygenated flavanone. The $^1$HNMR spectrum also showed the presence of a methoxyl (δ3.71), four hydroxyl groups [8.45 (3×OH), 12.61 (chelated)], and an aromatic two-proton singlet (δ6.09). Furthermore, the $^1$H and $^{13}$CNMR spectral data showed the presence of a δ,δ-dimethylallyl and a lavandulyl group. in the EI-mass spectrum, fragment ion peaks were observed at m/z 140 due to ring B, and m/z 382 and 381 to ring A. The $^1$H and $^{13}$CNMR spectra based on the ring B moiety were almost superimposable on those of kenukanones D and E which have a 2′,6′-dihydroxy-4′-methoxyl substitution. Consequently, the ring B moiety methoxyl substitution. Consequently, the ring B moiety in Fr4-1-1 is 2′,6′-dihydroxy-4′-methoxy and the γ,γ-dimethylallyl and the lavandulyl groups are substituted at C-6 and C-8, respectively, on the ring A. The positions of the γ,γ-dimethylallyl and the lavandulyl group were elucidated as follows. In the $^{13}$C-$^1$H long range COSY, a chelated hydroxyl group at C-5 correlated with three carbons at 160.3 (C-5), 108.4 (C-6) and 103.3 (C-10) through $^2$J and $^3$, respectively. On the other hand, methylene protons at δ3.33 assigned to those of the γ,γ-dimethylallyl group caused a cross peak with C-6 carbon through $^2$J. The protons also correlated with δ160.3 (C-5) and 162.4 (C-7) through $^3$J. Consequently, the γ,γ-dimethylallyl group was substituted at C-6, and the lavandulyl was at C-8. Based on the CD data (Experimental), the configuration of C-2 is S. Hence, Fr4-1-1 is (2S)-6-γ,γ-dimethylallyl-5′,7,2′,6′-tetrahydroxy-8-lavandulyl-4′-methoxyflavanone. The formula of which is as follows.

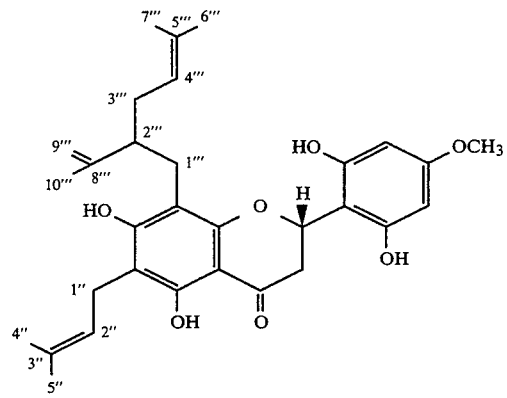

Inventors named this new compound as "Exiguaflavanone D" for *Sophora exigua*.

The spectral data of Exiguaflavanone D is as follows:
EIMS m/z (rel. int.): 522 (10), 399 (88), 383 (6), 382 (26), 281 (100), 325 (67), 259 (12), 203 (31), 177 (48), 167 (12), 166 (5), 140 (10).

HRMS m/z: [M+]+ 522.2597 (Calcd. 522.2617 for $C_{31}H_{38}O_7$). CDΔε$_{281}$ −5.9 (negative max.), Δε$_{305}$ +1.5 (positive max.). UV (nm, MeOH): 296, 348.

$^1$H NMR (acetone-d$_6$) δ: 1.49, 1.55, 1.62, 1.65, 1.75 (3H each, br s, Me), 2.00–2.56 (5H, m, H-1‴, 2‴ and 3‴), 2.51 (1H, dd, J=17, 3 Hz, H-3 eq), 3.33 (2H, br d, J=7 Hz, CH$_2$, H-9″), 4.97 (1H, t like, CH=, H-4‴), 5.17 (1H, t like, CH=, H-2″), 5.93 (1H, dd, J=14, 3 Hz, H-2), 6.09 (2H, s, H-3′ and 5′), 8.45 (3H, 3×OH), 12.61 (1H, C$_5$-OH).

$^{13}$C NMR (CDCl$_3$) δ: 17.9 (C-5″, 6‴), 19.4 (C-10‴), 21.8 (C-1″), 25.8 (C-7‴), 25.9 (C-4″), 28.2 (C-1‴), 31.7 (C-3‴), 41.2 (C-3), 47.8 (C-2‴), 55.3 (OMe), 73.6 (C-2), 94.6 (C-3′, 5′), 103.3 (C-10), 105.0 (C-1′), 107.5 (C-8), 108.4 (C-6), 111.2 (C-9‴), 123.5 (C-2″), 124.5 (C-4″), 131.7 (C-5‴), 132.1 (C-3″), 149.2 (C-8‴), 158.5 (C-2′, 6′), 160.3 (C-5), 160.4 (C-9), 162.3 (C-4′), 160.4 (C-9), 162.4 (C-7), 199.3 (C-4).

In the above structure, the groups attached to rings A and B are considered to be responsible for activity and the residue on ring A in the formula is considered to be involved in the coupling with MRSA as binding side. It is also considered that the two hydroxyl groups and one ether group on ring B are active sides.

As a medicinal substance, the compound of the invention can be administered orally in such dosage forms as capsules, tablets and on. The compound can also be administered externally in the form of, for example, an ointment. Thus, the compound of the invention can be administered in the same manner as the conventional antibiotics. Moreover, a synergistic or additive effect may be obtained by using the compound of the invention in combination with other anti-MRSA agents.

The compound of the present invention is an unmodified principle of the root of *Sophora exigua*, a shrub native to Thailand. Meanwhile, *Sophora exigua* has for centuries been used in folk medicine by natives in Thailand against respiratory diseases and as anti-pyretic. Consequently, it is not only free from acute toxicity but also is remotely toxic chronically.

It is evident from the forgoing disclosure that the compound of the invention is not only remarkably active against MSSA but also against MRSA. Consequently, the use of the compound of the invention as a drug should bring forth a considerable benefit to man infected by these microorganisms.

Furthermore, since the compound is a secondary metabolite of plant life, the expression of resistance may be effectively precluded.

What is claimed is:

1. An anti-MRSA compound comprising the formula:

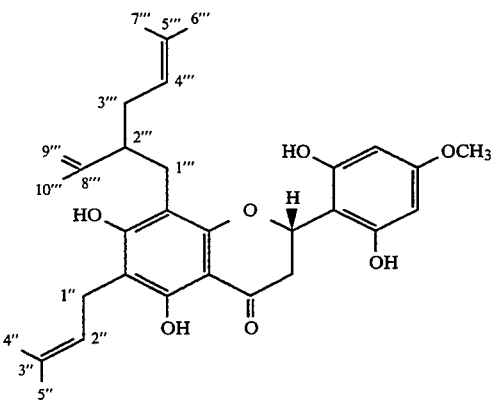

in a substantially pure form.

* * * * *